US00PP25786P2

(12) United States Plant Patent
Meerow

(10) Patent No.: US PP25,786 P2
(45) Date of Patent: Aug. 4, 2015

(54) ***HIPPEASTRUM* PLANT NAMED 'JAX'**

(50) Latin Name: ***Hippeastrum* Herb.**
Varietal Denomination: Jax

(71) Applicant: The United States of America, as represented by the Secretary of Agriculture, Washington, DC (US)

(72) Inventor: Alan W Meerow, Davie, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 129 days.

(21) Appl. No.: 13/987,802

(22) Filed: Sep. 4, 2013

(51) Int. Cl.
*A01H 5/02* (2006.01)

(52) U.S. Cl.
USPC ..... Plt./402

(58) Field of Classification Search
USPC ..... Plt./402
CPC ..... A01H 5/025; A01H 5/02; A01H 5/00
See application file for complete search history.

*Primary Examiner* — Kent L Bell
(74) *Attorney, Agent, or Firm* — Gail E. Poulos; John D. Fado; Lesley Shaw

(57) ABSTRACT

A new and distinct diploid (2n=22) *Hippeastrum* interspecific hybrid plant named 'JAX' particularly characterized by semi-pendant trumpet-shaped flowers, measuring approximately 15-16 cm long, approximately 12-13.5 cm wide laterally, approximately 4-16 cm wide dorsal-ventrally, and with a unique color pattern of lightly striated amethyst (closest RHS Color Chart is red-purple 73A) on a white (RHS 155D) background, most prominently on the lateral inner tepals, with a picotee of the same color.

3 Drawing Sheets

Latin name of the genus and species of the plant claimed: 'Jax' is a new Amaryllis plant that is a *Hippeastrum* Herb.

Variety denomination: The Amaryllis plant claimed is of the variety denominated 'Jax', *Hippeastrum* hybrid Herb.

BACKGROUND OF THE INVENTION

The present invention is a new and distinct interspecific hybrid of *Hippeastrum* Herb., commonly known as amaryllis, a member of the family Amaryllidaceae, and is henceforth referred to by the cultivar name Jax.

'Jax' originated as a cross made by the inventor in 2001 as part of a breeding program in Miami, Fla., USA. The objectives of the breeding program are to develop new amaryllis varieties with novel floral form and coloration and heat tolerance. The female parent is an F1 interspecific hybrid (*H. ambiguum*×*H. papilio* clone 4-16, unpatented). The pollen parent is an unnamed plant of *H. brasilianum*.

The new cultivar was selected on the basis of its trumpet floral shape and unique color pattern. Over the course of seven years of evaluation, 'Jax' has shown excellent heat resistance, as has its parents, grown under ambient conditions in Miami, Fla. under 50% shade, and resistance to Red Scorch fungus (*Staganospora curtisii*).

Asexual reproduction of the new cultivar by twin-scale cuttings taken in a controlled environment in Miami, Fla. has shown that the unique features of this new amaryllis are stable and reproduced true to type in successive generations.

SUMMARY OF THE INVENTION

The following traits have been repeatedly observed and are determined to be the unique characteristics of 'Jax'. It is contrasted with its parents in Table 1. These characteristics in combination distinguish 'Jax' as a new and distinct cultivar:

1) Trumpet-shaped flower.
2) Striations and picotee of amethyst color (closest match RHS Color Chart is red-purple 73A), characterized using a Nikon CR-400 colorimeter with the CIELAB color space (Gonnet 1993, 1998) in the range of L*(C)=80-82, a*(C)=10-13, b*(C)=2.2-2.8.
3) 'Jax' shows resistance to Red Scorch fungus (*Staganospora curtisii*) and high temperatures (30-35° C.), as do its parents.

TABLE 1

Comparison of *Hippeastrum* 'Jax' and its two parent plants.

| Characteristic | 'Jax' | Clone 4-16 | Unnamed plant of *H. brasilianum* |
|---|---|---|---|
| No. scapes per season | 2-3 | 2-3 | 2 |
| Scape height (cm) | 40-65.7 | 50-55 | 50-55 |
| No. firs. Per scape | 4-6 | 2-4 | 2-3 (4) |
| Flr color | amethyst on white | red-purple on white | white |
| Floral fragrance | None | None | Present |

Of the numerous commercial cultivars of amaryllis familiar to the inventor, the most similar to the new *Hippeastrum* 'Jax' is *Hippeastrum* 'Sampa' (U.S. Plant Pat. No. 12,526), from which 'Jax' differs by its unique sub-pendent trumpet-shaped flower, light amethyst striations on the tepals, undulate tepal margins, and fewer flowers on the scape ('Sampa' bears 6-8 flowers per umbel).

BRIEF DESCRIPTION OF THE PHOTOGRAPHS

DETAILED BOTANICAL DESCRIPTION

The cultivar 'Jax' has not been observed under all possible environmental conditions. The phenotype may vary somewhat with variations in environment such as temperature, daylength and light intensity, without, however, any variance in genotype.

Color descriptions below are based on evaluations with a Minolta CR-400 colorimeter at CIE D65/2$^0$ illumination/viewer conditions. The color parameters correspond to the uniform color space CIELAB, derived from Gonnet (Journal of Horticultural Science, Volume 68,499-510, 1993; Food Chemistry, Volume 63,409-415, 1998). Two color coordinates, a* and b*, as well as a psychometric index of lightness, L*, are defined. The L* is a measurement of luminosity, i.e., the equivalence of each color on the gray scale, ranging from 0 (black) to 100 (white). The a* takes positive values (0 to +60) for reddish colors and negative values (0 to −60) for the greenish ones, whereas the b* takes positive values (0 to +60) for yellowish colors and negative values (0 to −60) for the bluish ones. This is much more precise and repeatable analysis of color than obtained by using color charts (Ayala-Silva and Meerow, Proc. Intl. Trop. Hort. Soc., Volume 50, 138-144, 2006). The colorimeter takes three consecutive measurements of each sample, which was repeated three times, thus each set of color coordinates obtained are means of nine measurements. Where a reasonably close match could be discerned, The R.H.S. Colour Chart (Royal Horticultural Society, London, England, 1966) is also referenced.

TABLE 2

Colorimeter readings under the CIELAB color space for various locations on the flowers of *Hippeastrum* hybrid 'Jax'. See text for explanation of the values.

Figure 1B:
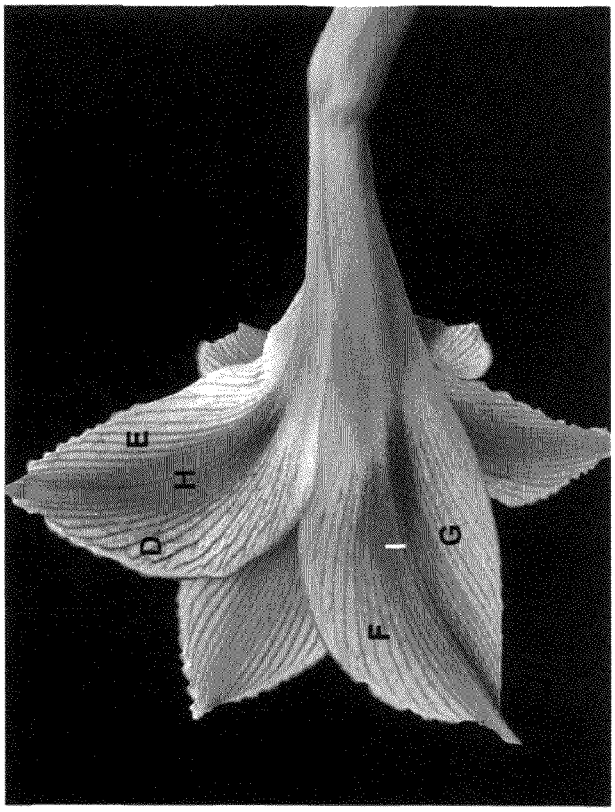
FIG. 1A and FIG. 1B are gray scale photographs of the flowers of *Hippeastrum* hybrid 'Jax' showing the locations of colorimeter readings in Table 2 below.
Figure 1A:
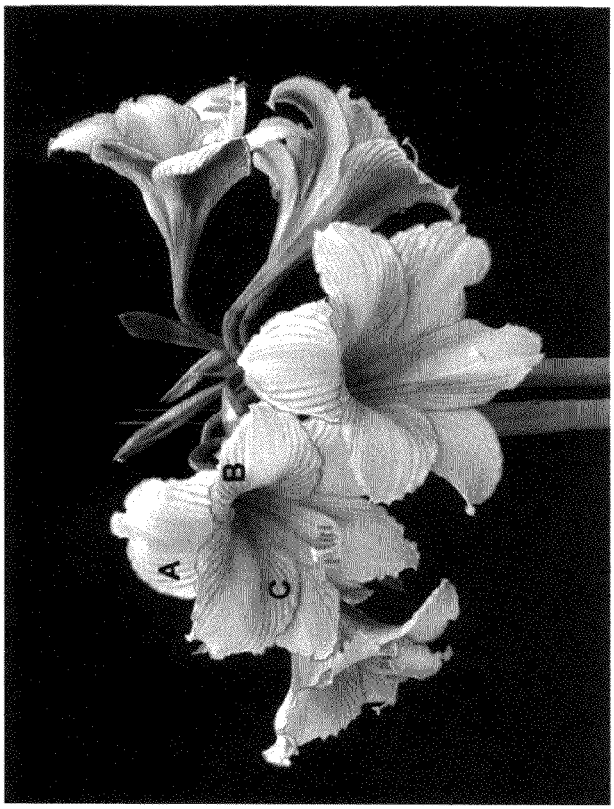
Figure 2:
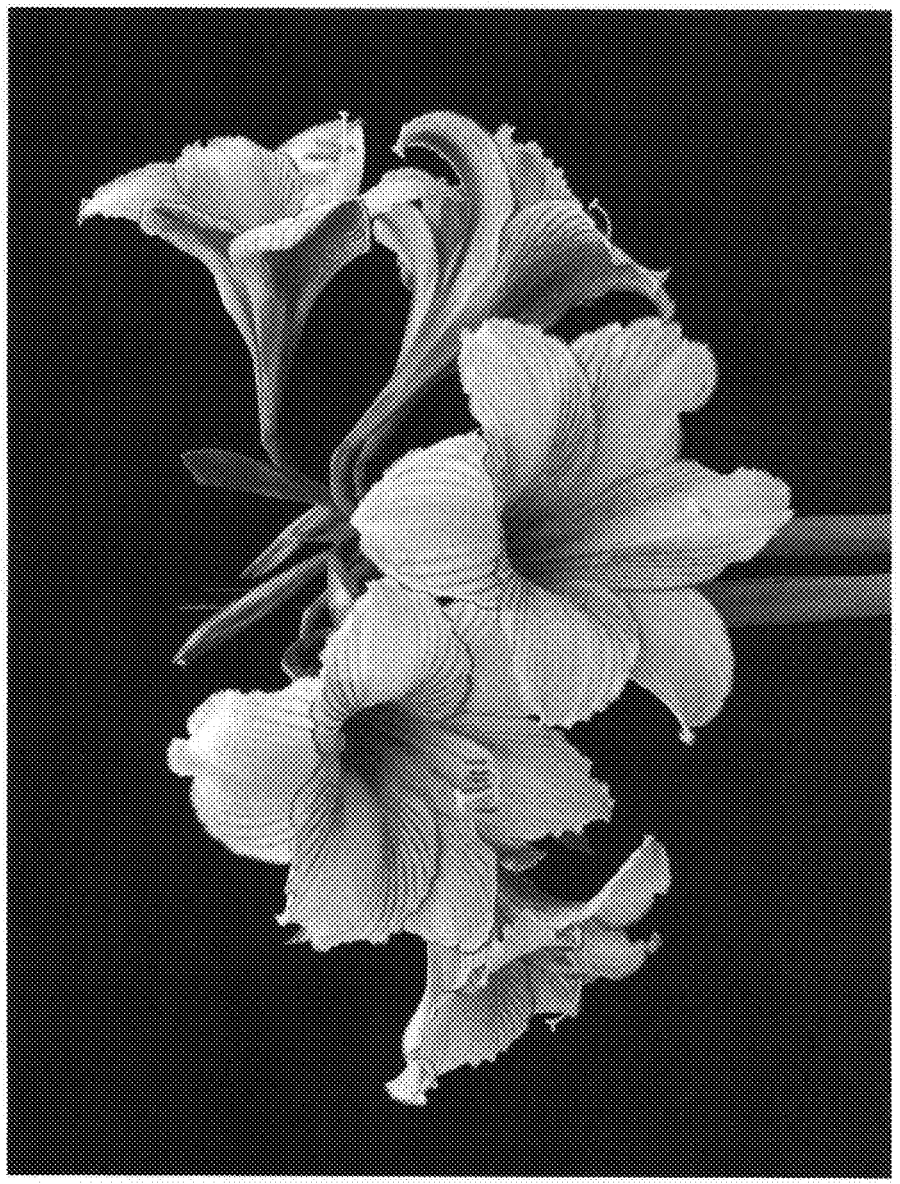
FIG. 2 and FIG. 3 are photographs of the flower of *Hippeastrum* hybrid 'Jax'.
Figure 3:
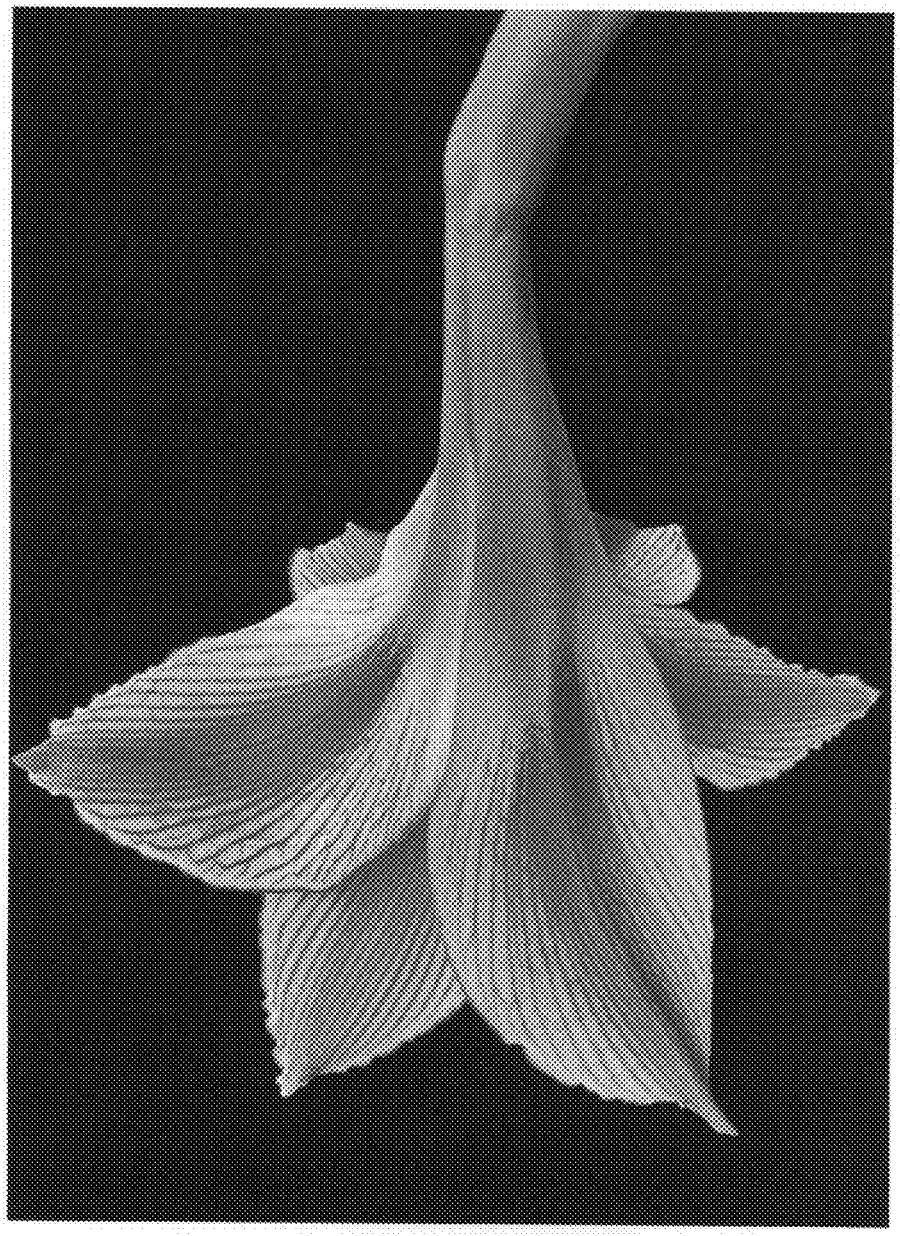

| Location (see FIG. 1) | | L*(C) | a*(C) | b*(C) |
|---|---|---|---|---|
| A | MEAN | 81.97 | 9.82 | 2.83 |
| | STDEV | 1.68 | 0.94 | 0.18 |
| B | MEAN | 84.19 | 11.14 | 2.60 |
| | STDEV | 3.94 | 2.99 | 1.07 |
| C | MEAN | 78.28 | 13.69 | 1.22 |
| | STDEV | 5.20 | 5.40 | 1.76 |
| D | MEAN | 74.56 | 19.17 | −0.39 |
| | STDEV | 0.31 | 0.05 | 0.04 |
| E | MEAN | 81.84 | 7.52 | 3.16 |
| | STDEV | 0.48 | 0.04 | 0.02 |
| F | MEAN | 82.55 | 13.39 | 1.89 |
| | STDEV | 6.86 | 6.60 | 2.56 |
| G | MEAN | 67.80 | 26.44 | −2.09 |
| | STDEV | 3.90 | 4.37 | 2.05 |
| H | MEAN | 62.74 | 28.23 | 1.63 |
| | STDEV | 0.11 | 0.05 | 0.02 |
| I | MEAN | 61.47 | 31.65 | −0.46 |
| | STDEV | 5.67 | 4.19 | 1.55 |

Botanical classification: *Hippeastrum* hybrid cultivar 'Jax'.

Parentage:

*Female or seed parent*.—Proprietary selection of *Hippeastrum ambiguum*×*H. brasilianum* identified as code number 8-16, not patented.

*Male or pollen parent*.—Unnamed plant of *Hippeastrum brasilianum*.

Propagation:

*Type*.—Twin-scale cuttings (division of the mother bulb into vertical segments and twin-scale units).

*Time to initiate roots, summer*.—About 30 days at temperatures of about 30° C.

*Time to initiate roots, winter*.—About 40 days at temperatures of about 22° C.

*Time to develop roots, summer*.—About 65 days at temperatures of about 30° C.

*Time to develop roots, winter*.—About 90 days at temperatures of about 22° C.

Plant description:

*Appearance*.—Perennial herbaceous amaryllis. Upright and clumping growth habit, moderately dwarf.

*Crop time*.—From bulb scale cuttings, about two years are required to produce a finished, flowering plant in a 15 to 20-cm container.

*Vigor*.—Moderately vigorous.

*Plant height*.—About 60 cm.

*Plant spread*.—About 45 cm.

Roots: White; numerous; fine and fibrous to moderately thick and fleshy; produced from basal plate of bulb; freely branching.

Bulb:

*Diameter*.—About 5-6 cm, increasing to about 8-11 cm with age.

*Circumference*.—About 16 cm, increasing to 35 cm.

*Shape*.—Ovoid.

*Color*.—RHS 149A; tunic, RHS 165A.

*Offsets produced per year*.—One to two offsets per bulb.

Foliage description:

*Arrangement*.—Distichous.

*Quantity*.—4-8 per bulb.

*Length, mature leaves*.—64-65 cm.

*Width, mature leaves*.—About 5.3 cm.

*Shape*.—Lorate.

*Apex*.—Obtuse.

*Margin*.—Entire.

*Texture*.—Coarse; glabrous.

*Color*.—Young foliage, upper surface: RHS 144A. Young foliage, lower surface: RHS 144B. Mature foliage, upper surface: L*(C)=37.67, a*(C)=−14.45, b*(C)=19.36. Mature foliage, lower surface: L*(C)=40.46, a*(C)=−15.16, b*(C)=21.00.

Flower description:

*Appearance*.—Trumpet-shaped single flowers arranged in umbels borne on a leafless scape. Corolla and calyx similar (tepals), three-parted and fused at the base. Freely flowering, typically about four (up to six) open flowers per scape and about 8-12 flowers and flower buds per plant. Flowers last about three or four days each. Flowers persistent. Flowers held slightly pendant from scape.

*Flowering response*.—Plants flower in the spring. Plants typically flower about March 15 to April 15 in Miami, Fla.

*Fragrance*.—Not detected.

*Scape*.—Length: 35-45 cm. Diameter: About 1.5 cm. Appearance/aspect: Leafless; upright; not fasciated, hollow. Strength: Moderate. Texture: Smooth. Color: RHS137D.

*Pedicel*.—7.5 to 9.5 cm long.

*Flower length*.—15-16 cm.

*Flower diameter*.—About 13 cm.

*Flower depth* (*height*).—About 15 cm.

*Flower buds*.—Length: about 4 cm. Width: about 1 cm. Shape: Oblanceolate. Color: close to RHS155D in lower half, RHS 73A in upper half. Rate of flower bud opening: about 2 days each, all flower opening in 8-10 days.

*Tepals*.—Number: six, in two whorls of 3. Fused and forming tube in proximal ⅓. Outer whorl: Length: 12.5-14.5 cm. Width: 4.5-6 cm. Shape: Elliptic. Apex: Apiculate. Margin: Entire; undulate. Texture: Smooth; tetals appear luminous and crystalline. Color: Both surfaces: ground color, white, close to RHS155D; lightly overlain with amethyst (Table 2, red-purple RHS73A) striations on either side of keel; keel of free tepal deeply colored red-purple RHS 73A, green at throat of tube (RHS yellow-green RHS 149A); marginal picotee, RHS 73A. Inner whorl — Shape: elliptic. Apex: apiculate. Margin: undulate. Color: both surfaces: ground color, white, close to RHS155D; overlain lightly with red-purple-red RHS 73A striations on either side of keel, green (yellow-green RHS 149A, at basal ⅔; marginal pictotee, RHS 73A.

*Throat*.—Green, RHS 149A yellow-green, no fimbrae or hairs.

*Reproductive organs*.—Androecium: Stamen number: Six. Length: 9.5-11 cm. Filaments white (RHS 155D white) for most of length, green, RHS 151B yellow-green, in proximal 5 cm. Anther shape: Elliptic. Anther size: About 8 mm. Anther color: white, RHS 155B white. Pollen amount: Moderate. Pollen color: yellow, RHS 7A yellow. Gynoecium: Pistil number: One. Pistil length: About 12.5 cm. Stigma shape: tri-lobed. Stigma width: about 8 mm. Stigma color: white, RHS 155D. Style length: 13.5-14 cm. Style color: white, RHS 155D hite, for most of length, green, RHS 151B, in proximal 5 cm. Ovary shape: ellipsoid, ovary length: 22-34 mm, ovary width: 8-11.5 mm, ovary color: RHS141C.

*Seed*.—Seed development has not been observed.

Chromosome number: 2n=22. Plant is diploid.

Disease resistance: Plants of the new amaryllis appear resistant to Red Scorch Fungus (*Staganospora curtisii*).

Heat tolerance: Plants of the new amaryllis have demonstrated good tolerance to high temperatures about 30 to 35° C.

We claim:

1. A new and distinct cultivar of amaryllis plant (genus *Hippeastrum*) named 'Jax', as illustrated and described.

* * * * *